(12) United States Patent
Weigand et al.

(10) Patent No.: US 10,647,852 B2
(45) Date of Patent: May 12, 2020

(54) PHOTOCHROMIC MULTIPLE RING-FUSED NAPHTHOPYRANS HAVING EXTREME LONGWAVE ABSORPTION EXTENDING FAR INTO THE VISIBLE WAVELENGTH RANGE

(71) Applicant: RODENSTOCK GMBH, München (DE)

(72) Inventors: Udo Weigand, München (DE); Herbert Zinner, Rohrbach (DE)

(73) Assignee: RODENSTOCK GMBH (DE)

( * ) Notice: Subject to any disclaimer, the term of this patent is extended or adjusted under 35 U.S.C. 154(b) by 0 days.

(21) Appl. No.: 16/336,185

(22) PCT Filed: May 23, 2017

(86) PCT No.: PCT/EP2017/000617
§ 371 (c)(1),
(2) Date: Mar. 25, 2019

(87) PCT Pub. No.: WO2018/054507
PCT Pub. Date: Mar. 29, 2018

(65) Prior Publication Data
US 2019/0284397 A1    Sep. 19, 2019

(30) Foreign Application Priority Data

Sep. 26, 2016    (DE) .......... 10 2016 011 559

(51) Int. Cl.
| | | |
|---|---|---|
| C09B 57/00 | (2006.01) | |
| G02B 1/04 | (2006.01) | |
| G02B 5/23 | (2006.01) | |
| C07D 293/04 | (2006.01) | |
| C07D 493/14 | (2006.01) | |
| C07D 495/04 | (2006.01) | |
| C07D 493/04 | (2006.01) | |

(52) U.S. Cl.
CPC ............ *C09B 57/00* (2013.01); *C07D 493/04* (2013.01); *C07D 493/14* (2013.01); *C07D 495/04* (2013.01); *G02B 1/041* (2013.01); *G02B 5/23* (2013.01)

(58) Field of Classification Search
CPC .......... C09B 57/00; G02B 1/041; G02B 5/23; C07D 495/04; C07D 493/04; C07D 493/14
See application file for complete search history.

(56) References Cited

U.S. PATENT DOCUMENTS

| | | | |
|---|---|---|---|
| 3,567,605 A | 3/1971 | Becker | |
| 2006/0228557 A1* | 10/2006 | Kim ..................... | C07D 311/78 428/411.1 |

FOREIGN PATENT DOCUMENTS

| | | |
|---|---|---|
| EP | 0792468 A1 | 9/1997 |
| EP | 0906366 A1 | 4/1999 |
| EP | 0912908 A1 | 5/1999 |
| EP | 0946536 A1 | 10/1999 |
| EP | 1119560 A1 | 8/2001 |
| EP | 2178883 A1 | 4/2010 |
| EP | 2457915 A1 | 5/2012 |
| EP | 2471794 A1 | 7/2012 |
| EP | 2655354 A1 | 10/2013 |
| EP | 2684886 A1 | 1/2014 |
| EP | 2760869 A1 | 8/2014 |
| EP | 2788340 A1 | 10/2014 |
| EP | 2829537 A1 | 1/2015 |
| EP | 2872517 A1 | 5/2015 |
| EP | 3010924 A1 | 4/2016 |
| JP | 2017036248 A * | 2/2017 |
| WO | 9748993 A1 | 12/1997 |
| WO | 2009024271 A1 | 2/2009 |
| WO | 2012084231 A1 | 6/2012 |
| WO | 2013045086 A1 | 4/2013 |
| WO | 2013083282 A1 | 6/2013 |

OTHER PUBLICATIONS

JP-2017036248-A; WIPO English machine translation; accessed Aug. 9, 2019; p. 1-26.*
Translation of the International Search Report dated Sep. 22, 2017; International Patent Application No. PCT/EP2017/000617 filed May 23, 2017. ISA/EP.

* cited by examiner

*Primary Examiner* — John M Mauro
(74) *Attorney, Agent, or Firm* — McDonald Hopkins LLC

(57) ABSTRACT

The present invention relates to photochromic polyfused naphthopyrans having very long-wave absorption of the closed form extending well into the visible wavelength range, and to the use thereof in all kinds of plastics, especially for ophthalmic purposes, preferably in driving glasses.

12 Claims, 2 Drawing Sheets

Figure 1:
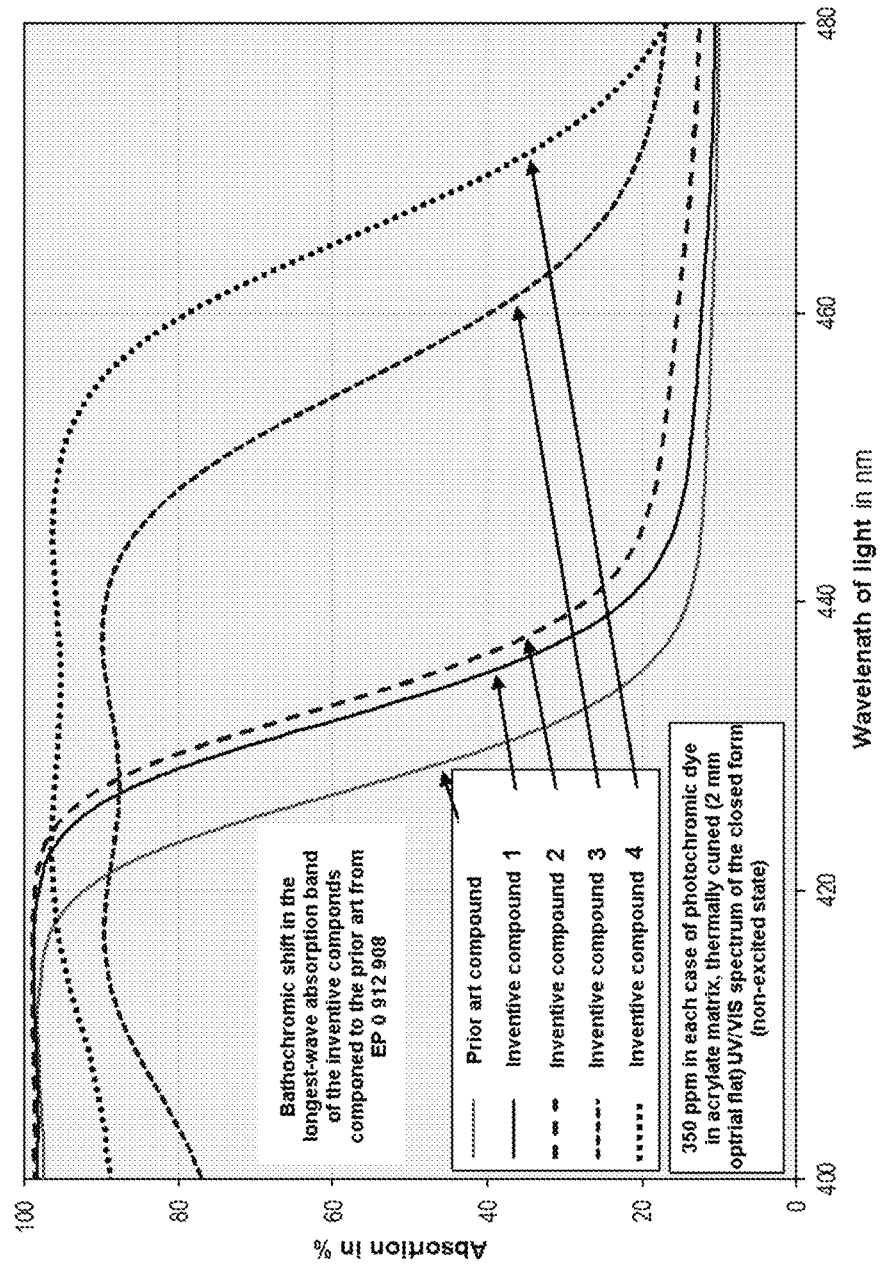

PHOTOCHROMIC MULTIPLE RING-FUSED NAPHTHOPYRANS HAVING EXTREME LONGWAVE ABSORPTION EXTENDING FAR INTO THE VISIBLE WAVELENGTH RANGE

CROSS-REFERENCE TO RELATED APPLICATION

This application is a 35 U.S.C. 371 national stage filing of PCT Application No. PCT/EP2017/000617 filed on May 23, 2017, entitled "PHOTOCHROMIC MULTIPLE RING-FUSED NAPHTHOPYRANS HAVING EXTREME LONGWAVE ABSORPTION EXTENDING FAR INTO THE VISIBLE WAVELENGTH RANGE," which claims priority to German Patent Application No. 10 2016 011 559.9, filed on Sep. 26, 2016, each of which are incorporated herein in their entirety by reference.

The present invention relates to photochromic polyfused naphthopyrans having very long-wave absorption of the closed form extending far into the visible wavelength range, and to the use thereof in all kinds of plastics, especially for ophthalmic purposes, preferably in driving glasses. The compounds of the invention additionally have a very good lifetime combined with very high performance.

Various classes of dye that reversibly change color on irradiation with light for particular wavelengths, especially solar rays, have long been known. The reason for this is that these dye molecules are converted by light energy to an excited state ("open form"), which they leave again when the energy supply is stopped and return to their ground state. These photochromic dyes include various pyran systems that have already been described in the prior art with different base systems and substituents.

Pyrans, especially naphthopyrans and larger ring systems derived from these, are currently the most studied class of photochromic compounds. Even though the first patent was filed as early as 1966 (U.S. Pat. No. 3,567,605), it was not until the 1990s that compounds that seemed suitable for use in spectacle glasses were developed. A suitable compound class of pyrans is that of the 2,2-diaryl-2H-naphtho[1,2-b]pyrans or the 3,3-diaryl-3H-naphtho[2,1-b]pyrans which, in excited form, have various darkening colors from yellow to red.

Great interest attaches to the fused naphthopyrans derived from these base systems that have longer-wave absorption owing to this larger ring system and result in red, violet and blue darkening colors. This purpose is typically accomplished using a benzene ring having an additional bridge in the ortho position (in the compounds of the invention hereinafter the bridge with the $R_1$ and $R_2$ substituents).

If—as in the compounds of the present invention below—there is a metallic bridge, the result is a five-membered ring fused to the naphthopyran. Examples can be found in EP 0 792 468 and EP 0 906 366 for a bridging carbon atom ("indenonaphthopyrans") and in EP 0 946 536 for a bridging oxygen atom.

EP 2 457 915, EP 2 471 794, EP 2 684 886, EP 2 788 340 and EP 2 872 517 disclose compounds in which at least one further ring system is fused to the core indenonaphthopyran structure, but, by contrast with the inventive compounds of the formula (I) below, to the C—C bond between the $R_7$ and $R_{10}$ substituents, i.e. to another point in the core structure. However, the fusion to this point results in a distinctly smaller bathochromic shift of the longest-wave absorption band compared to the inventive compounds of the formula (I) below.

Among the compounds detailed in EP 0 912 908 are compounds in which two further ring systems are fused to the core indenonaphthopyran structure, i.e. in the same place as in the inventive compounds of the formula (I) below. However, the effect of the fusions described (benzofuro, benzothieno and indolo) by comparison with the inventive compounds of the formula (I) is a distinctly smaller bathochromic shift in the longest-wave absorption band of the closed form.

If, by contrast, there is a diatomic bridge, the result is a six-membered ring fused to the naphthopyran. Compounds having a bridge composed of two carbon atoms are described in EP 1 119 560; cf. also EP 2 829 537 or EP 3 010 924.

EP 1 097 156 describes compounds having a diatomic bridge composed of a carbon atom and an oxygen atom, as do EP 2 178 883 and EP 2 760 869.

However, the various photochromic dyes available to date in the prior art do not show long-wave absorption of the closed form that extends well into the violet or blue visible wavelength range. What would be enabled by the latter would be that spectacle glasses configured with such photochromic dyes would no longer require any, or would require barely any, UV light for the transition to the excited (colored) form and in this respect, therefore, darkening of such spectacle glasses could also be achieved, for example, behind a completely UV-absorbing automobile windshield.

It is therefore an object of the present invention to provide photochromic dyes that are to feature one-wave absorption of the closed form that extends well into the violet or blue visible wavelength range.

This object is achieved by the subject-matter characterized in the claims.

More particularly, photochromic polyfused naphthopyrans of the general formulae (I), (II) and (III) are provided:

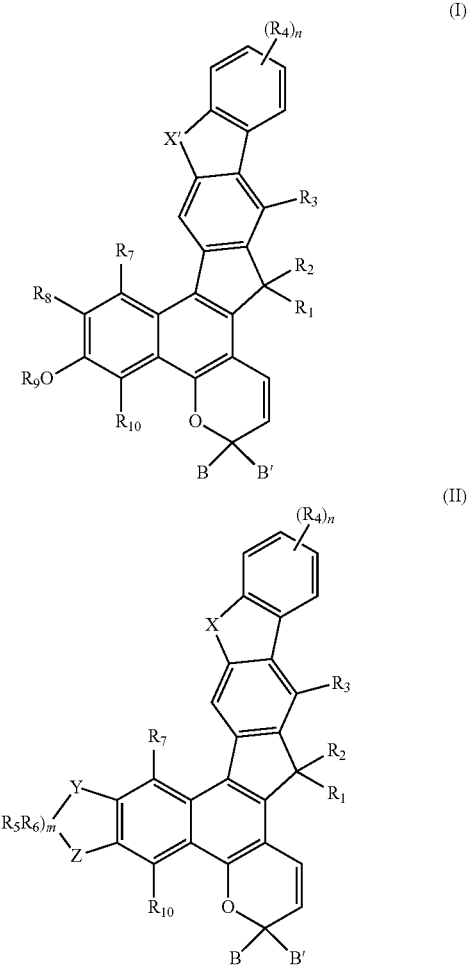

-continued (III)

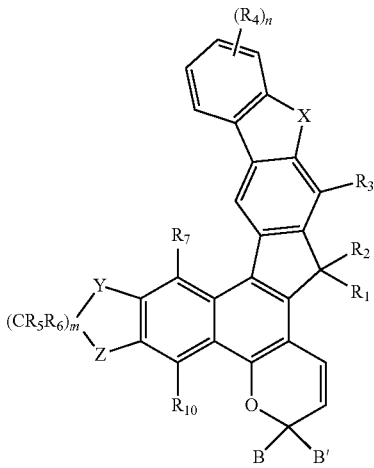

in which the $R_1$, $R_2$, $R_3$, $R_4$, $R_7$, $R_8$ and $R_{10}$ radicals each independently represent a substituent selected from the group α consisting of a hydrogen atom, a $(C_1-C_{18})$-alkyl radical, a $(C_3-C_7)$-cycloalkyl radical that may have one or more heteroatoms, for example O or S, a $(C_1-C_{15})$-thioalkyl radical, a $(C_1-C_{15})$-alkoxy radical, a hydroxyl group, a trifluoroethyl group, bromine, chlorine, fluorine, an un-, mono- or disubstituted phenyl, phenoxy, benzyl, benzyloxy, naphthyl or naphthoxy radical, where these substituents may in turn be selected from the group β consisting of a hydrogen atom, a $(C_1-C_6)$-alkyl radical, a $(C_3-C_7)$-cycloalkyl radical, a $(C_1-C_6)$-thioalkyl radical, a $(C_1-C_6)$-alkoxy radical, a phenyl radical, a benzyl radical or a naphthyl radical;
n represents an integer from 1 to 4;
or the $R_1$ and $R_2$ radicals together with the carbon atom bonded to these radicals form a three- to eight-membered carbo- or heteromonocyclic ring which optionally bears one or more substituents from group β, and to which one to three aromatic or heteroaromatic ring systems may be fused, where the ring system(s) is/are independently selected from benzene, naphthalene, phenanthrene, pyridine, quinoline, furan, thiophene, pyrrole, benzofuran, benzothiophene, indole and carbazole, which may in turn be substituted by one or more substituents selected from group β;
or two adjacent $R_4$ radicals form a fused benzene ring which may be un-, mono- or disubstituted, where the substituents may be selected from group β;
or two adjacent $R_4$ radicals form a 1,1-dimethylindene or benzofuran ring system fused via the double bond in the five-membered ring;
or two adjacent $R_4$ radicals form a 2H-chromene or 1H-isochromene ring system via the double bond in the heterocyclic six-membered ring,
the $R_5$ and $R_6$ radicals each independently represent a substituent selected from hydrogen, a $(C_1-C_{18})$-alkyl radical, a phenyl radical, a benzyl radical or a naphthyl radical;
m represents an integer from 1 to 4, preferably 1 or 2, more preferably 2;
or two adjacent —$CR_5R_6$— moieties form a fused benzene ring which may be un-, mono- or disubstituted, where the substituents may be selected from group β;
the $R_9$ radical represents a substituent selected from hydrogen, a $(C_1-C_{18})$-alkyl radical, a phenyl radical, a benzyl radical or a naphthyl radical;
X' in the formula (I) is selected from —$SO_2$—, —$CH_2$—, —$C(CH_3)_2$—, —$C(C_2H_5)_2$—, —$C(C_6H_5)_2$—, —O—$CH_2$—, —$CH_2$—O—, —$CH_2$—$CH_2$—, —$C(CH_3)_2$—$CH_2$— or —$CH_2$—$C(CH_3)_2$—,
X in the formula (II) or (III) is selected from —O—, —S—, —$SO_2$—, —$NC_6H_5$—, —$CH_2$—, —$C(CH_3)_2$—, —$C(C_2H_5)_2$—, —$C(C_6H_5)_2$—, —O—$CH_2$—, —$CH_2$—O—, —O—(C=O)—, —(C=O)—O—, —$CH_2$—$CH_2$—, —$C(CH_3)_2$—$CH_2$— or —$CH_2$—$C(CH_3)_2$—,
Y and Z are independently selected from —O—, —S—, —$SO_2$—, —$N(C_1-C_6)$-alkyl-, —$NC_6H_5$—, —$CH_2$—, —$C(CH_3)_2$—, —$C(C_2H_5)_2$— or —$C(C_6H_5)_2$—, where Y or Z, optionally together with the respectively adjacent $CR_5R_6$ moiety, may form a fused benzene ring which may be un-, mono- or disubstituted, where the substituents may in turn be selected from group β, or Y or Z together with the respectively adjacent $CR_5R_6$ moiety form a fused naphthalene, 9,9-dimethylfluorene or dibenzofuran ring system which may in turn be substituted by one or more substituents selected from group β;
and in which B and B' are independently selected from one of the following groups a) and b), where
a) is a mono-, di- and trisubstituted aryl radical, where the aryl radical is phenyl, naphthyl or phenanthryl, and
b) an un-, mono- and disubstituted heteroaryl radical, where the heteroaryl radical is selected from pyridyl, furanyl, thienyl, benzofuranyl, benzothienyl, 1,2,3,4-tetrahydrocarbazolyl or julolidinyl;
where the substituents of the aryl and heteroaryl radicals in a) and b) are selected from group β or the —(O—$CHR_{13}$—$CH_2)_q$—$OR_{14}$ moiety where $R_{13}$ represents hydrogen or a methyl radical, $R_{14}$ represents hydrogen or a $(C_1-C_6)$-alkyl radical and q represents an integer from 1 to 50;
or the substituents in a) and b) are selected from group χ consisting of amino, mono-$(C_1-C_{18})$-alkylamino, di-$(C_1-C_{18})$-alkylamino, phenethenyl un-, mono- or disubstituted on the phenyl ring, un-, mono- or disubstituted (phenylimino)methylene, un-, mono- or disubstituted (phenylmethylene)imino and un-, mono- or disubstituted mono- and diphenylamino, piperidinyl, 3,5-dimethylpiperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono-, di- or trisubstituted 9,10-dihydroacridinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenz[b,f]azepinyl, where the substituent(s) may in turn independently be selected from group β;
or two directly adjacent substituents of the aryl and heteroaryl radicals in a) and b) constitute a V—$(CR_{11}R_{12})_p$—W moiety where p represents an integer from 1 to 3, the $R_{11}$ and $R_{12}$ radicals each independently represent a substituent selected from β, and V and W are independently selected from —O—, —S—, —$N(C_1-C_6)$-alkyl-, —$NC_6H_5$—, —$CH_2$—, —$C(CH_3)_2$—, —$C(C_2H_5)_2$— or —$C(C_6H_5)_2$—;
or two or more adjacent $CR_{11}R_{12}$ moieties are part of a fused benzene ring which may be un-, mono- or disubstituted, where the substituents may in turn be selected from group β;
or V and/or W together with the respectively adjacent $CR_{11}R_{12}$ moiety form a fused benzene ring which may be un-, mono- or disubstituted, where the substituents may in turn be selected from group β.

It is a feature of the compounds of the invention that two further ring systems are fused to the C—C bond in the benzene ring adjacent to the $R_3$ substituent in a core indenonaphthopyran structure. As a consequence, the longest-wave absorption band of the closed form of these photochromic dyes undergoes such a bathochromic shift that it extends well into the violet or blue visible wavelength range. For the transition to the excited (covered) form, the compounds of the invention, as a result, by contrast with conventional photochromic dyes available in the prior art, no longer require any UV light, or require barely any, and therefore darken, for example, even behind an automobile windshield that completely absorbs UV light. It is thus possible to implement, for example, driving glasses that darken significantly even in a closed car when the sun shines directly through the completely UV-absorbing windshield.

The compounds of the invention are therefore notable for their excellent UV hardening compatibility; in other words—introduced, for example, into an acrylate monomer matrix with UV initiator—they withstand free-radical polymerization of the matrix triggered by intense UV light without damage. Moreover, they have a very good lifetime combined with very high performance. They are usable in all kinds of plastic.

The molecular structure of the compounds of the invention is based on a core indenonaphthopyran structure (in each case with the substituents $R_1$, $R_2$, $R_3$, $R_7$ and $R_{10}$ in the formulae) containing the photolabile pyran unit (with the substituents B and B'). This is responsible for the photochromic character since light excitation reversibly breaks the bond between the oxygen of the pyran unit and the carbon atom with the B and B' substituents, which gives rise to a colored merocyanine system.

As already set out above, the present invention is based on the surprising finding that, in the case of multiple fusion to the core indenonaphthopyran structure, the longest-wave absorption band of the closed form of the photochromic compounds of the invention can be shifted bathochromically so far that it extends well into the violet or blue visible wavelength range. This state of affairs was achievable in two ways.

Firstly, compounds of the formula (I) that have fusion of at least two further ring systems (with X' and the $R_4$ substituents) to the C—C bond of the benzene ring adjacent to the $R_3$ substituent. With X' specifically selected from —SO$_2$—, —CH$_2$—, —C(CH$_3$)$_2$—, —C(C$_2$H$_5$)$_2$—, —C(C$_6$H$_5$)$_2$—, —O—CH$_2$—, —CH$_2$—O—, —CH$_2$—CH$_2$—, —C(CH$_3$)$_2$—CH$_2$— or —CH$_2$—C(CH$_3$)$_2$—, in the compounds of the formula (I)—by comparison with the prior art from EP 0 912 908—the longest-wave absorption band of the closed form is distinctly bathochromically shifted.

Secondly, compounds of the formulae (II) and (III) are provided, which additionally have a further fusion of at least one ring system (with Y and Z and the $R_5$ and $R_6$ substituents) to the C—C bond between the $R_7$ and $R_{10}$ substituents. These polyfused indenonaphthopyrans have extremely long-wave and intense absorption bands of the closed form.

The long-wave absorption of the closed form of the compounds of the invention well into the visible wavelength range naturally entails a yellow initial color of these photochromic dyes. In order to conceal this initial color in the uses, it is possible as desired to add violet or blue permanent dyes as known in the prior art, which then give rise to neutral gray initial colors together with the compounds of the invention.

In one embodiment of the invention, the $R_1$, $R_2$, $R_3$, $R_4$, $R_7$, $R_5$ and $R_{10}$ radicals are each independently selected from a hydrogen atom, a (C$_1$-C$_6$)-alkyl radical or a (C$_3$-C$_7$)-cycloalkyl radical.

In a further embodiment of the present invention, X' in the formula (I) is selected from —CH$_2$—, —C(CH$_3$)$_2$—, —C(C$_2$H$_5$)$_2$—, —C(C$_6$H$_5$)$_2$—, —O—CH$_2$— or —CH$_2$—O—.

In another embodiment of the present invention, X in the formula (II) or (III) is selected from —O—, —S—, —CH$_2$—, —C(CH$_3$)$_2$—, —C(C$_2$H$_5$)$_2$—, —C(C$_6$H$_5$)$_2$—, —O—CH$_2$—, —CH$_2$—O—, —CH$_2$—CH$_2$—, —C(CH$_3$)$_2$—CH$_2$— or —CH$_2$—C(CH$_3$)$_2$—.

In a further embodiment of the present invention, Y and Z are independently selected from —O—, —CH$_2$—, —C(CH$_3$)$_2$—, —C(C$_2$H$_5$)$_2$— or —C(C$_6$H$_5$)$_2$—, where Y or Z may in turn optionally form, together with respectively adjacent CR$_5$R$_6$ moiety, a fused benzene ring which may be un-, mono- or disubstituted, where the substituents may in turn be selected from group β.

The $R_9$ radical is preferably a (C$_1$-C$_{18}$)-alkyl radical, a phenyl radical or benzyl radical.

In a preferred embodiment of the present invention, the B and B' radicals are independently selected from group a), as defined above.

Irrespective of the above, in one embodiment of the present invention, the photochromic polyfused naphthopyrans of the invention have the general formula (I).

For measurement of the spectral and photochromic properties of the compounds of the invention, 350 ppm in each case of the photochromic dye were dissolved in an acrylate monomer matrix and thermally polymerized with the aid of a temperature program after addition of a polymerization initiator.

The photochromic darkening properties ("saturation absorption of the open form"; see Tab. 1) of the specimen is thus produced was then ascertained according to DIN EN ISO 8980-3.

FIG. 1 shows the absorption spectra (400-480 nm) of inventive compounds in the closed form (non-excited state) compared to the prior art from EP 0 912 908.

The molecular structure of the compounds shown in FIG. 1 is detailed in table 1 below. Inventive compounds 1 and 2 are described by the formula (IV) below, inventive compound 3 by the formula (VI) below, and inventive compound 4 by the formula (V) below.

The longest-wave absorption band of the closed form of the compounds of the invention is shifted significantly toward longer wavelengths compared to the prior art.

As a result, the compounds of the invention still undergo good darkening even behind a completely UV-absorbing automobile windshield (see table 1).

In order to quantify this, the measurements of the darkening properties were conducted once without ("standard") and once with an upstream longpass filter (see table 1). The longpass filter used (GG400; from Schott) completely absorbs the UV component of the excitation light, which achieves a good simulation of the conditions behind an automobile windshield.

TABLE 1

Comparison of the saturation absorptions of the open form (excited state):
Standard measurement to DIN EN ISO 8980-3 vs. measurement with GG400 filter

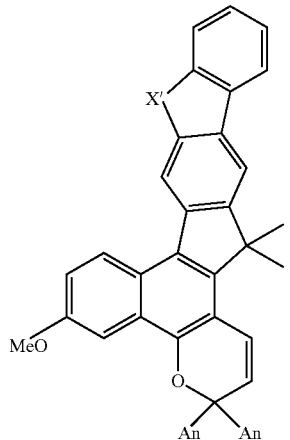

(IV)

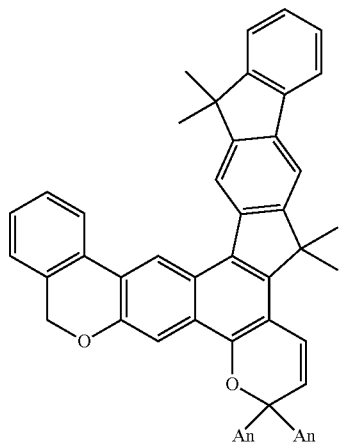

(V)

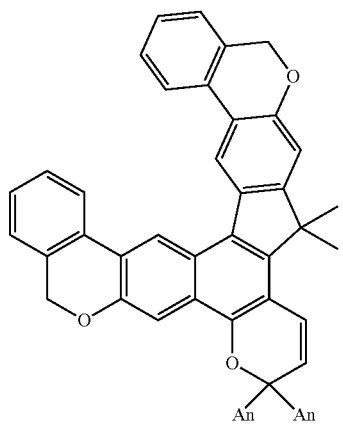

(VI)

| | X' in formula (IV) | Wavelength with 50% absorption (closed form; see FIG. 1) | Saturation absorption 23° C. (open form) Standard measurement | Saturation absorption 23° C. (open form) Measurement with GG400 filter | Difference in saturation absorptions (standard − GG400) |
|---|---|---|---|---|---|
| State of the art form EP 0 912 908 (formula (IV)) | S | 428 nm | 88% | 77% | 11% |
| Inventive compound 1 (formula (IV)) | $CMe_2$ | 433 nm | 87% | 81% | 6% |

TABLE 1-continued

| | | | | | |
|---|---|---|---|---|---|
| Inventive compound 2 (formula (IV)) | CH$_2$—O | 435 nm | 87% | 82% | 5% |
| Inventive compound 3 (formula (VI)) | | 457 nm | 84% | 80% | 4% |
| Inventive compound 4 (formula (V)) | | 467 nm | 86% | 84% | 2% |

(An = anisyl, i.e. 4-methoxyphenyl radical)

The difference in the saturation absorptions between the standard measurement (without GG400 filter) and the measurement with GG400 filter is a meaningful parameter. The smaller this difference, the less UV light below 400 nm is required for the darkening and the more the photochromic dye is suitable for use in driving glasses. The compounds of the invention all have a distinctly smaller difference value compared to prior art compounds and require virtually no UV light below 400 nm for darkening.

Figure 2:
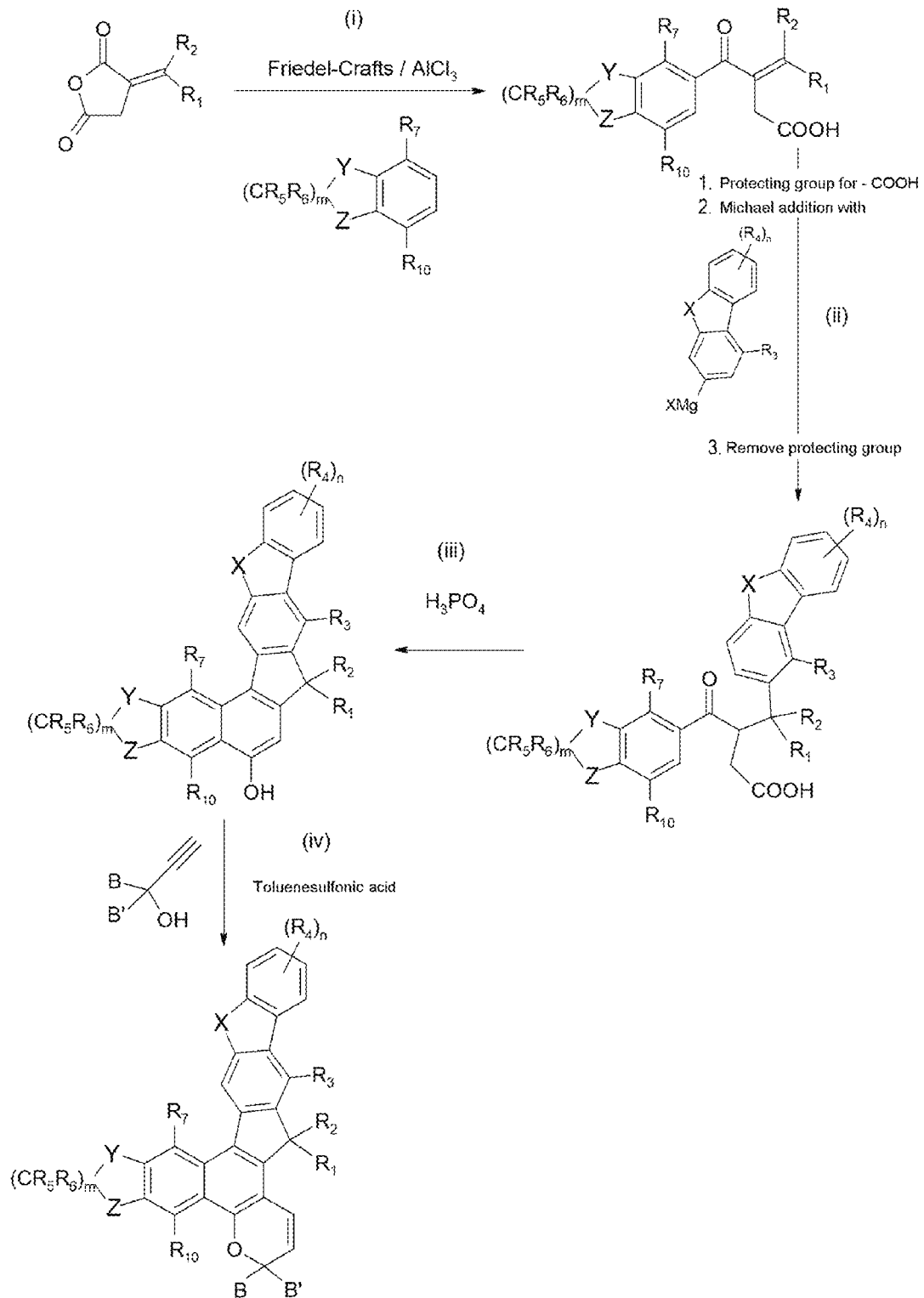

For synthesis of the compounds of the invention (see synthesis scheme according to FIG. 2), suitably substituted methylidenesuccinic anhydrides are subjected in a first step to a Friedel-Crafts reaction with suitably substituted aromatic systems (step (i)). The —COOH group of the resulting intermediate is then protected and this intermediate is subjected to a Michael addition with appropriately substituted aryl Grignard compounds (step (ii)). After the carboxylic acid protecting group has been removed, via intramolecular cyclization by means of phosphoric acid, correspondingly substituted naphthol derivatives are formed (step (iii)). Subsequently, these are reacted with suitably substituted 2-propyn-1-ol derivatives in step (iv) to give the compounds of the invention.

The compounds of the invention may be used in plastic materials or plastic articles of any type and form for a multitude of end uses for which photochromic characteristics are important. It is possible here to use one dye according to the present invention or a mixture of such dyes. For example, the photochromic naphthopyran dyes of the invention can be used in lenses, especially ophthalmic lenses, lenses for all kinds of spectacles, for example ski goggles, sunglasses, motorcycle goggles, visors of protective helmets and the like, especially in driving glasses. In addition, the photochromic naphthopyrans of the invention can also be used, for example, as sun protection in vehicles and living spaces in the form of windows, protective shades, covers, roofs or the like.

For production of such photochromic articles, the photochromic naphthopyrans of the invention, by various methods described in the prior art, as already specified in WO 99/15518, may be applied to or embedded into a polymer material, such as an organic plastic material.

A distinction is made here between what are called bulk coloring and surface coloring methods. A bulk coloring method comprises, for example, the dissolving or dispersing of the photochromic compound or compounds according to the present invention in a plastic material, for example by the addition of the photochromic compound(s) to a monomeric material prior to the polymerization. A further means of producing a photochromic article is the penetration of the plastic material(s) with the photochromic compound(s) by immersing the plastic material into a hot solution of the photochromic dye(s) according to the present invention or else, for example, a thermal transfer method. The photochromic compound(s) may also be provided, for example, in the form of a separate layer between adjacent layers of the plastic material, for example as part of a polymeric film. In addition, applying of the photochromic compound(s) as part of a coating present on the surface of the plastic material is also possible. The expression "penetrating" shall be understood to mean the migration of the photochromic compound(s) into the plastic material, for example through the solvent-assisted transfer of the photochromic compound(s) into a polymer matrix, vapor phase transfer or other surface diffusion operations of this kind. Advantageously, such photochromic articles, for example spectacle glasses, can be produced not just by means of the standard bulk coloring, but in the same way also by means of surface coloring, where the latter variant can achieve surprisingly lower migration. This is advantageous particularly in the case of subsequent finishing layers since—for example in the case of an antireflection coating, as a result of the lower reverse diffusion under reduced pressure—layer detachments and similar defects are significantly reduced.

Overall, on the basis of the photochromic naphthopyrans of the invention, it is possible to apply colorings of any degree of compatibility (from a chemical point of view and in respect of color), i.e. dyes, to the plastic material or embed them into it in order to satisfy both esthetic features and medical or fashion aspects. The dye(s) specifically selected may accordingly vary depending on the intended effects and requirements.

The invention claimed is:

1. Photochromic polyfused naphthopyrans having the formulae (I), (II) and (III):

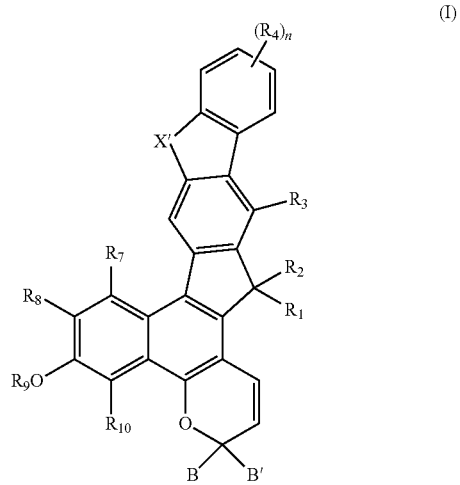

(I)

-continued

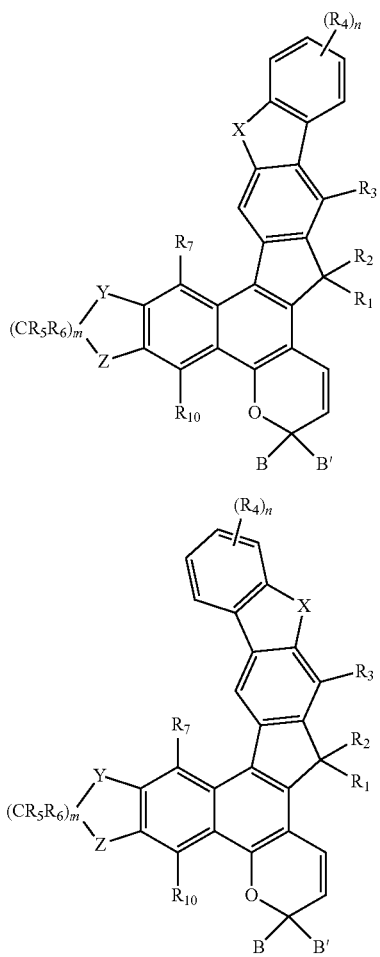

(II)

(III)

in which the $R_1$, $R_2$, $R_3$, $R_4$, $R_7$, $R_8$ and $R_{10}$ radicals each independently represent a substituent selected from the group α consisting of a hydrogen atom, a $(C_1\text{-}C_{18})$-alkyl radical, a $(C_3\text{-}C_7)$-cycloalkyl radical that may have one or more heteroatoms, a $(C_1\text{-}C_{18})$-thioalkyl radical, a $(C_1\text{-}C_{18})$-alkoxy radical, a hydroxyl group, a trifluoromethyl group, bromine, chlorine, fluorine, an un-, mono- or disubstituted phenyl, phenoxy, benzyl, benzyloxy, naphthyl or naphthoxy radical, where these substituents may in turn be selected from the group β consisting of a hydrogen atom, a $(C_1\text{-}C_6)$-alkyl radical, a $(C_3\text{-}C_7)$-Cycloalkyl radical, a $(C_1\text{-}C_6)$-thioalkyl radical, a $(C_1\text{-}C_6)$-alkoxy radical, a phenyl radical, a benzyl radical or a naphthyl radical;

n represents an integer from 1 to 4;

or the $R_1$ and $R_2$ radicals together with the carbon atom bonded to these radicals form a three- to eight-membered carbo- or heteromonocyclic ring which optionally bears one or more substituents from group β, and to which one to three aromatic or heteroaromatic ring systems may be fused, where the ring system(s) is/are independently selected from benzene, naphthalene, phenanthrene, pyridine, quinoline, furan, thiophene, pyrrole, benzofuran, benzothiophene, indole and carbazole, which may in turn be substituted by one or more substituents selected from group β;

or two adjacent $R_4$ radicals form a fused benzene ring which may be un-, mono- or disubstituted, where the substituents may be selected from group β;

or two adjacent $R_4$ radicals form a 1,1-dimethylindene or benzofuran ring system fused via the double bond in the five-membered ring;

or two adjacent $R_4$ radicals form a 2H-chromene or 1H-isochromene ring system via the double bond in the heterocyclic six-membered ring, the $R_5$ and $R_6$ radicals each independently represent a substituent selected from hydrogen, a $(C_1\text{-}C_{18})$-alkyl radical, a phenyl radical, a benzyl radical or a naphthyl radical;

m represents an integer from 1 to 4;

or two adjacent $-CR_5R_6-$ moieties form a fused benzene ring which may be un-, mono- or disubstituted, where the substituents may be selected from group β;

the $R_9$ radical represents a substituent selected from hydrogen, a $(C_1\text{-}C_{18})$-alkyl radical, a phenyl radical, a benzyl radical or a naphthyl radical;

X' in the formula (I) is selected from $-SO_2-$, $-CH_2-$, $-C(CH_3)_2-$, $-C(C_2H_5)_2-$, $-C(C_6H_5)_2-$, $-O-CH_2-$, $-CH_2-O-$, $-CH_2-CH_2-$, $-C(CH_3)_2-CH_2-$ or $-CH_2-C(CH_3)_2-$;

X in the formula (II) or (III) is selected from $-O-$, $-S-$, $-SO_2-$, $-N(C_1\text{-}C_6)$-alkyl-, $-NC_6H_5-$, $-CH_2-$, $-C(CH_3)_2-$, $-C(C_2H_5)_2-$, $-C(C_6H_5)_2-$, $-O-CH_2-$, $-CH_2-O-$, $-O-(C=O)-$, $-(C=O)-O-$, $-CH_2-CH_2-$, $-C(CH_3)_2-CH_2-$ or $-CH_2-C(CH_3)_2-$;

Y and Z are independently selected from $-O-$, $-S-$, $-SO_2-$, $-N(C_1\text{-}C_6)$-alkyl-, $-NC_6H_5-$, $-CH_2-$, $-C(CH_3)_2-$, $-C(C_2H_5)_2-$ or $-C(C_6H_5)_2-$, where Y or Z, optionally together with the respectively adjacent $CR_5R_6$ moiety, may form a fused benzene ring which may be un-, mono- or disubstituted, where the substituents may in turn be selected from group β, or Y or Z together with the respectively adjacent $CR_5R_6$ moiety form a fused naphthalene, 9,9-dimethylfluorene or dibenzofuran ring system which may in turn be substituted by one or more substituents selected from group β;

and in which B and B' are independently selected from one of the following groups a) and b), where a) is a mono-, di- or trisubstituted aryl radical, where the aryl radical is phenyl, naphthyl or phenanthryl, and b) is an un-, mono- or disubstituted heteroaryl radical, where the heteroaryl radical is selected from pyridyl, furanyl, thienyl, benzofuranyl, benzothienyl, 1,2,3,4-tetrahydrocarbazolyl or julolidinyl;

where the substituents of the aryl and heteroaryl radicals in a) and b) are selected from group β or the $-(O-CHR_{13}-CH_2)_q-OR_{14}$ moiety where $R_{13}$ represents hydrogen or a methyl radical, $R_{14}$ represents hydrogen or a $(C_1\text{-}C_6)$-alkyl radical and q represents an integer from 1 to 50;

or the substituents in a) and b) are selected from group x consisting of amino, mono-$(C_1\text{-}C_{18})$-alkylamino, di-$(C_1\text{-}C_{18})$-alkylamino, phenethenyl un-, mono- or disubstituted on the phenyl ring, un-, mono- or disubstituted (phenylimino)methylene, un-, mono- or disubstituted (phenylmethylene)imino and un-, mono- or disubstituted mono- and diphenylamino, piperidinyl, 3,5-dimethylpiperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono-, di- or trisubstituted 9,10-dihydroacridinyl, un-, mono- or disubstituted 1,2,3,4- tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenz[b,f]azepinyl, where the substituent(s) may in turn independently be selected from group β;

or two directly adjacent substituents of the aryl and heteroaryl radicals in a) and b) constitute a V—$(CR_{11}R_{12})_p$—W moiety where p represents an integer from 1 to 3, the $R_{11}$ and $R_{12}$ radicals each independently represent a substituent selected from β, and V and W are independently selected from —O—, —S—, —N($C_1$-$C_6$)-alkyl-, —$NC_6H_5$—, —$CH_2$—, —$C(CH_3)_2$—, —$C(C_2H_5)_2$— or —$C(C_6H_5)_2$—;

or two or more adjacent $CR_{11}R_{12}$ moieties are part of a fused benzene ring which may be un-, mono- or disubstituted, where the substituents may in turn be selected from group β;

or V and/or W together with the respectively adjacent $CR_{11}R_{12}$ moiety form a fused benzene ring which may be un-, mono- or disubstituted, where the substituents may in turn be selected from group β.

2. Photochromic polyfused naphthopyrans as claimed in claim 1, where the $R_1$, $R_2$, $R_3$, $R_4$, $R_7$, $R_8$ and $R_{10}$ radicals are each independently selected from a hydrogen atom, a ($C_1$-$C_6$)-alkyl radical or a ($C_3$-$C_7$)-cycloalkyl radical.

3. Photochromic polyfused naphthopyrans as claimed in claim 1, where X' in the formula (I) is selected from —$CH_2$—, —$C(CH_3)_2$—, —$C(C_2H_5)_2$—, —$C(C_6H_5)_2$—, —O—$CH_2$— or —$CH_2$—O—.

4. Photochromic polyfused naphthopyrans as claimed in claim 1, where X in the formula (II) or (III) is selected from —O—, —S—, —$CH_2$—, —$C(CH_3)_2$—, —$C(C_2H_5)_2$—, —$C(C_6H_5)_2$—, —O—$CH_2$—, —$CH_2$—O—, —$CH_2$—$CH_2$—, —$C(CH_3)_2$—$CH_2$— or —$CH_2$—$C(CH_3)_2$—.

5. Photochromic polyfused naphthopyrans as claimed in claim 1, where Y and Z are independently selected from —O—, —$CH_2$—, —$C(CH_3)_2$—, —$C(C_2H_5)_2$— or —$C(C_6H_5)_2$—, where Y or Z, optionally together with the respectively adjacent $CR_5R_6$ moiety, may form a fused benzene ring which may be un-, mono- or disubstituted, where the substituents may in turn be selected from group β.

6. Photochromic polyfused naphthopyrans as claimed in claim 1, where the $R_9$ radical is a ($C_1$-$C_{18}$)-alkyl radical, a phenyl radical or a benzyl radical.

7. Photochromic polyfused naphthopyrans as claimed in claim 1, where the B and B' radicals are independently selected from group a) as defined above.

8. Photochromic polyfused naphthopyrans as claimed in claim 1, having the general formula (I).

9. Photochromic polyfused naphthopyrans as claimed in claim 1, having the general formula:

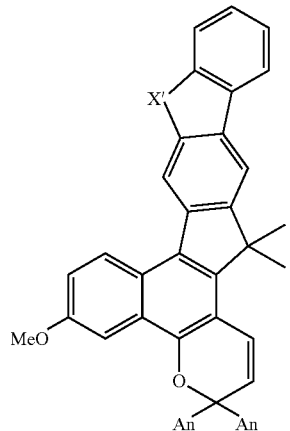

(IV)

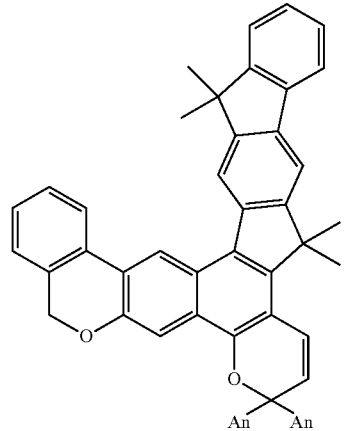

(V)

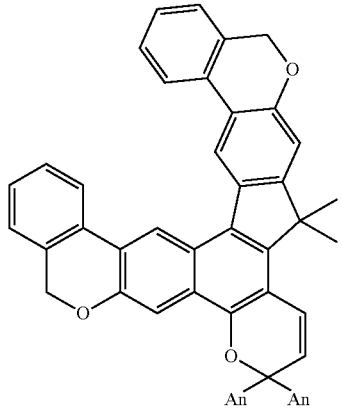

(VI)

where X' is as defined above;
where An is an anisyl.

10. A plastic material comprising one or more of the photochromic polyfused naphthopyrans as claimed in claim 1.

11. The plastic material in claim 10, wherein the plastic material is an ophthalmic lens.

12. The plastic material in claim 10, wherein the plastic material is an ophthalmic lens for driving glasses.

* * * * *